(12) United States Patent
Roush et al.

(10) Patent No.: US 10,603,322 B2
(45) Date of Patent: Mar. 31, 2020

(54) THERAPEUTIC TARGETING OF CASEIN KINASE 1δ IN BREAST CANCER

(71) Applicant: The Scripps Research Institute, La Jolla, CA (US)

(72) Inventors: William R. Roush, Jupiter, FL (US); Derek R. Duckett, Jupiter, FL (US); John L. Cleveland, Land O' Lakes, FL (US); Laura H. Rosenberg, Illford (GB)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 15/768,257

(22) PCT Filed: Oct. 5, 2016

(86) PCT No.: PCT/US2016/055436
§ 371 (c)(1),
(2) Date: Apr. 13, 2018

(87) PCT Pub. No.: WO2017/066055
PCT Pub. Date: Apr. 20, 2017

(65) Prior Publication Data
US 2018/0311252 A1  Nov. 1, 2018

Related U.S. Application Data

(60) Provisional application No. 62/240,689, filed on Oct. 13, 2015.

(51) Int. Cl.
*A61K 31/5377* (2006.01)
*A61P 35/00* (2006.01)
*C12Q 1/6886* (2018.01)

(52) U.S. Cl.
CPC ......... *A61K 31/5377* (2013.01); *A61P 35/00* (2018.01); *C12Q 1/6886* (2013.01); *C12Q 2600/136* (2013.01)

(58) Field of Classification Search
None
See application file for complete search history.

(56) References Cited

U.S. PATENT DOCUMENTS

2014/0200207 A1   7/2014  Calabrese et al.
2015/0274729 A1 * 10/2015  Roush .................. C07D 473/16
                                           514/210.21

FOREIGN PATENT DOCUMENTS

WO   WO 2013/130461   *  9/2013  .............. A01N 43/90

OTHER PUBLICATIONS

"International Application Serial No. PCT/US2016/055436, International Search Report dated Jan. 6, 2017", 2 pgs.
"International Application Serial No. PCT/US2016/055436, Written Opinion dated Jan. 6, 2017", 4 pgs.

* cited by examiner

*Primary Examiner* — Alicia L Otton
(74) *Attorney, Agent, or Firm* — Hugh Wang; Thomas Fitting (57) ABSTRACT

The invention provides a method of inhibiting casein kinase 1δ (CK1δ), comprising contacting the CK1δ with a compound of formula (I), as defined herein; such as compound SR-3029. We demonstrate that CSNK1D is amplified and/or overexpressed in human breast tumors and that CK1δ can be medically targeted in human breast cancer subtypes overexpressing this kinase. The invention further provides a method of treating cancer, such as a breast cancer, melanoma, glioblastoma, medulloblastoma, renal, bladder or colon cancer, or a cancer that metastasizes to the brain, lung, or bone provided that both elevated CK1δ and β-catenin dependence are involved in those metastatic diseases. The cancer can be a breast cancer of the triple negative subclass of breast cancers (TNBC), or can be an HER+ breast cancer.

2 Claims, 6 Drawing Sheets

THERAPEUTIC TARGETING OF CASEIN KINASE 1δ IN BREAST CANCER

CROSS-REFERENCE TO RELATED APPLICATION

This application claims the priority of U.S. provisional application Ser. No. 62/240,689, filed Oct. 13, 2015, the disclosure of which is incorporated herein by reference in its entirety.

STATEMENT OF GOVERNMENT SUPPORT

This invention was made with government support under CA175094 from the National Institutes of Health. The government has certain rights in the invention.

BACKGROUND

Breast cancer accounts for nearly one quarter of all cancer diagnoses and is the principle cause of cancer-related mortality in women worldwide (1, 2). Currently, treatment selection for breast cancer is based on pathological information and histological grade, and on the expression status of the estrogen (ER), progesterone (PR) and epidermal growth factor 2 (HER2/neu) receptors, where targeted treatments blocking receptor function have made improvement in overall survival (1, 3). Indeed expression of ER and/or PR is a good prognostic factor and predictive indicator for benefit from endocrine therapies and although HER2 overexpression connotes adverse prognosis, patients greatly benefit from anti-HER2 targeted treatments (4, 5).

In contrast, the triple negative subclass of breast cancers (TNBC), defined by the absence of the ER and PR receptors and the lack of HER2 amplification, have no targeted treatment options, are highly aggressive and exhibit poor prognosis (6, 7). Although breast cancer research has pioneered and highlights the clinical benefits of targeted treatments, further identification of drivers and associated signaling pathways, particularly for TNBC and HER2 breast cancers, are needed to instruct the development of targeted therapies, to extend disease-free survival and improve the lives of cancer patients.

Casein kinase-1 delta (CK1δ) and epsilon (CK1ε) are two highly related serine/threonine kinases known to regulate diverse cellular processes, including circadian rhythm, membrane trafficking and the cytoskeleton, and both have been implicated in cancer (8-11). For example, myristolated CK1ε is sufficient to transform mammary epithelial cells in vitro whereas expression of a dominant-negative mutant of CK1δ impairs SV40-induced mammary carcinogenesis in vivo (12). As kinases CK1δ and CK1ε are eminently tractable for small molecule drug discovery. Nevertheless, the contribution of these kinases to human cancer is poorly understood and the non-selective nature of previously reported CK1δ/CK1ε inhibitors has impeded validation of these kinases as anti-cancer targets (9, 13-15). Indeed, pharmacological effects originally ascribed to inhibition of CK1δ/CK1ε are now known to be due to off-target action of the non-selective inhibitors employed (13, 16).

SUMMARY

This invention is directed, in various embodiments, to a method of inhibiting CK1δ, comprising contacting the CK1δ with an effective amount or concentration of a compound of formula (I)

(I)

wherein
each R is independently selected hydrogen or ($C_1$-$C_6$) alkyl, or two R groups bonded to a nitrogen atom together with the nitrogen atom can form a 5-7 membered heterocyclyl optionally further comprising 1 or 2 heteroatoms selected from the group consisting of O, S, and NR', wherein R' is hydrogen or ($C_1$-$C_6$)alkyl;

$Ar^1$ is an aryl or a 5-membered or 6-membered heteroaryl, which is unsubstituted or is substituted with 1-3 independently selected halo, ($C_1$-$C_6$)alkyl, ($C_1$-$C_6$)fluoroalkyl, ($C_1$-$C_6$)alkoxyl, cyano, nitro, C(=O)NR$_2$, OC(=O)NR$_2$, N(R) C(=O)OR, N(R)C(=O)R, or C(=O)OR;

$Het^1$ is a monocyclic or bicyclic heteroaryl, which is unsubstituted or is substituted with 1-3 independently selected halo, ($C_1$-$C_6$)alkyl, ($C_1$-$C_6$)fluoroalkyl, ($C_1$-$C_6$) alkoxyl, cyano, nitro, C(=O)NR$_2$, OC(=O)NR$_2$, N(R)C (=O)OR, N(R)C(=O)R, or C(=O)OR;

or a pharmaceutically acceptable salt thereof.

In various embodiments, the invention is directed to a method of treating cancer, including but not limited to breast cancer, melanoma, glioblastoma, medulloblastoma, renal, bladder and colon cancers. In addition, cancers like breast cancer that metastasize to the brain, lung, bone are also amenable to treatment with our CK1δ inhibitors, as long as both elevated CK1δ and β-catenin dependence are involved in those metastatic diseases. The method of treatment comprises administering to a patient afflicted therewith an effective dose of a compound of formula (I) as described above.

More specifically, the compound of formula (I) can be (SR-3029)

or a pharmaceutically acceptable salt thereof.

The invention further discloses that cancers particularly susceptible to treatment with CK1δ inhibitors are those cancers with upregulated expression levels of both CK1δ and β-catenin. Accordingly, in various embodiments the invention provides a method of identifying an anticancer drug effective for treatment of a cancer in a patient, comprising determining a level of CK1δ and a level of δ-catenin in the patient and selecting a CK1δ inhibitor for a treatment regimen if both the levels are elevated. Further, the invention provides a method of treating in a patient a breast cancer, a melanoma, a glioblastoma, a medulloblastoma, or a renal, bladder or colon cancer, or a cancer that metastasizes to the brain, lung, or bone, comprising determining if elevated CK1δ and β-catenin levels are present in the patient, and if both levels are elevated, selecting a CK1δ inhibitor for a treatment regimen.

In various embodiments, the invention provides a method of treatment of a triple negative subclass of breast cancers (TNBC). In other embodiments the invention provides a method of treatment of an HER+ breast cancer. The methods comprise administering an effective dose of a compound of formula (I) to a patient afflicted with the breast cancer.

BRIEF DESCRIPTION OF THE FIGURES

FIG. 1 | CK1δ is a clinically relevant and effective target for select breast cancer subtypes. (A) CK1δ mRNA expression in invasive ductal breast carcinomas (IDC) vs. adjacent normal tissue (*, p=6.78e-15). (B) Expression of CK1α1, CK1δ and CK1ε across PAM50 breast cancer subtypes based on RNA-Seq data (n=972 tumor samples, 113 solid tissue normal). Log 2 normalized read count (RSEM) is shown. (C) CSNK1D DNA copy number analyses in invasive breast carcinomas clustered according to CK1δ expression (n=303). Gene-level copy number estimates (GISTIC2 threshold): −2, −1, 0, 1, 2, representing homozygous deletion, single copy deletion, diploid normal copy, low-level copy number amplification, or high-level copy number amplification are shown. (D) Scatter plot of CSNK1D $Log_2$ mRNA expression vs. $Log_2$ copy number values (972 breast cancer patients). (E) CK1δ and CK1ε protein expression in indicated breast cancer cell lines and MCF10A mammary epithelial cells. (F) Chemical structure of SR-3029. (G) Anti-proliferative potency of SR-3029 in the indicated breast cancer cell lines. Data are plotted as % proliferation vs. vehicle (n=6). (H) Clonogenic growth and survival of indicated cells in the presence of SR-3029 or vehicle (n=3; p=0.0008). (I) Percent apoptosis by PI/Annexin V FACS following 72 hr treatment with indicated doses of SR-3029 (n=3; *, left to right p=0.0007 and 0.0001). (J) Left, Clonogenic growth of MDA-MB-231 cells overexpressing CK1δ or GFP+/−SR-3029 (n=3; *, p=0.001, , p=0.0035). Right, western blot confirming CK1δ overexpression +/−30 nM SR-3029 at 48 hr. (K) Relative growth (left; n=3, siδ1; p=0.01, siδ2; p=0.003) and percent cell death by trypan blue exclusion was measured (right; n=3, siδ1; p=0.01, siδ2 p=0.027) 5 days after transfection of MDA-MB-231 with non-targeting (NT) or CK1δ siRNAs. (L) qPCR data and immunoblot confirming knockdown of CK1δ but not CK1ε (n=3; ***, p<0.0001).

FIG. 2 | Inhibition of CK1δ/CK1ε Impairs orthotopic breast tumor growth in vivo. (A) Effects of CK1δ/CK1ε inhibitors on growth and establishment of MDA-MB-231-luc tumors monitored by luminescence intensity over time. Mice were treated once per day with SR-3029 or vehicle (10:10:80, DMSO:Tween-80:Water) at 20 mg/kg by i.p. injection. Arrow indicates start of treatment (n=8 for each cohort; , p=0.1). (B) Tumor size by luminescence and (C) comparison of gross tumor size at day 55. Representative tumors are shown. (D) Growth curves of indicated TNBC tumor models in mice treated with vehicle (black line) or SR-3029 (blue line) as above. Arrows indicate timing of first dose (n=8-10 for each cohort; , p=0.01; ***, p=0.0008). (E) TUNEL staining on serial sections of vehicle and SR-3029 treated MDA-MB-231 tumors (representative images are shown) (white line scale=200 μm). (F) Kaplan-Meier survival curves corresponding to studies shown in (D) (p-value calculated using log-rank test). (G) Body weight of mice treated daily with SR-3029 (blue line) or vehicle (black line) was followed for 8 weeks (n=8-10).

FIG. 3 | Silencing or inhibition of CK1δ provokes breast tumor regression and efficiently blocks growth of PDX breast models. (A) Left, qPCR data confirming efficient knockdown of CK1δ, but not of CK1ε transcripts, following 72 hr of treatment of MDA-MB-231-shCK1δ expressing cells with Dox (0.3 μg/ml) (n=3; *, p=0.0003). Right, corresponding CK1δ protein expression. (B) Cells expressing Dox inducible CK1δ or non-targeting (NT) shRNA were treated with 1 μg/ml Dox for 72 hr and transfected with vectors expressing CK1δ or GFP cDNA resistant to shRNA. Following a further 72 hours, percent cell death was measured by trypan blue exclusion in MDA-MB-231-shCK1δ (Black) and cells expressing non-targeting shRNAs (NT—white) (n=4; *, p=0.0001). (C) Growth of orthotopic MDA-MB-231-shCK1δ tumors in mice+/−Dox (administered ad lib in chow, 200 mg/kg), as monitored by caliper measurements (n=8 for each cohort; , p=0.006). Arrow indicates addition of Dox. (D) CK1δ knockdown in tumor tissue isolated from three independent mice, 7 days after Dox administration began. (E) Immunoblot comparing CK1δ expression in extracts of human normal breast or three independent BMC-4013 PDX tumors. (F) Growth curves of BCM-4013 PDX tumors in mice treated with vehicle (black line) or SR-3029 (blue line). Arrow indicates timing of first dose (n=12 for each cohort; *, p=0.0002). (G) Kaplan-Meier survival curve corresponding to studies shown in (F) (p-value calculated using log-rank test). (H) TUNEL staining on serial sections of vehicle and SR-3029 treated BMC-4013 tumors (representative images are shown) (white line scale=200 μm).

FIG. 4 | Modulation of the Wnt/β-catenin pathway is a biomarker for CK1δ activity and inhibition. (A) Wnt pathway genes significantly enriched in CK1δ overexpressing human breast tumors (fold change >2, p-value <0.05) (red is CK1δ gene). (B) Effect of SR-3029 (+) or vehicle (−) treatment (18 hr, 30 nM) on nuclear vs. cytoplasmic β-catenin in the indicated breast cancer cell lines. (C) Expression of active β-catenin (ABC) in MDA-MB-231 cells after 18 hr treatment with SR-3029 or vehicle or following transfection with CK1δ siRNAs (harvested at 48 hr). (D) Inhibition of TCF-dependent luciferase activity in MDA-MB-231 cells treated with increasing doses of SR-3029 for 6 hr or following 5 days treatment with 1 μg/ml Dox to activate expression of indicated shRNAs (n=3; *, p=0.013; ***, p=0.0002). (E) Effect of CK1δ inhibition (left, 24 hr treatment with 100 nM SR-3029) or knockdown (right, 48 hr after transfection) on expression of indicated proteins and (F) mRNAs by immunoblot or qPCR, respectively (n=3). (G) Expression of indicated mRNAs 24 hr after treatment with 100 nM SR-3029 (n=3; *, p<0.05; , p<0.01; *, p<0.001; SFRP1 p=0.0003; WNT3 p=0.001; WNT9A p=0.0007; MYC p=0.0271; CCND1 p=0.0054; CD44 p=0.0071). (H) TCF-dependent luciferase activity in HEK293T cells +/−CK1δ shRNA expression (+/−1 µg/ml Dox for 72 hr) followed by 3 hr treatment with 1 µg/ml Wnt-3a (*, p=7.23E-05 and 5.57E-06 left to right). (I) HEK293T cells stably expressing the TCF-dependent luciferase reporter were transfected with a control vector or a constitutively active (nuclear) mutant of β-catenin (S33Y) and incubated overnight +/−SR-3029 prior to addition of recombinant Wnt-3a (3 hr) (representative of 3 independent experiments is shown; *, p=0.0004 (left) and 0.0002 (right)). (J) Immunostaining for ABC expression (white line scale=200 µm). (K) Relative growth 4 days after infection of indicated cell lines with lentiviruses expressing either non-targeting (NT) or β-catenin shRNAs (n=3; Left to right; *, p=0.05, *, p=0.0009, *, p=0.001, ***, p=0.001) and corresponding western blots (right panel).

FIG. 5 | CK1δ is a necessary and sufficient driver of Wnt/β-catenin signaling in human breast cancer. (A) Cell growth (left) and apoptosis (right) measured after 72 hr+/−SR-3029 in MDA-MB-231 cells transfected with an empty vector or β-catenin-S33Y (n=4; *, p=0.05). (B) MDA-MB-231-shCK1δ cells treated with Dox (4 days, 1 µg/ml) were transfected with an empty vector or β-catenin-S33Y and cell number measured after 72 hr (n=3: ***, p=0.001). (C) Expression of nuclear and cytoplasmic β-catenin in MCF7 cells engineered to overexpress CK1δ or GFP. Bottom, quantification of nuclear β-catenin expression normalized to Histone H4 (n=3; *, p=0.02). (D) Immunostaining for ABC in MCF7 cells overexpressing CK1δ or GFP (white line scale=200 µm). (E) qPCR analysis of β-catenin targets in MCF7-CK1δ vs. MCF7-GFP cells (n=3; , p=0.01; *, p=0.001). (F) Immunoblot confirming CK1δ overexpression and increased cyclin-D1. (G) Effect of SR-3029 on clonogenic growth of MCF7 cells overexpressing CK1δ vs. GFP (n=6; Left to right; , p=0.01, , p=0.002). (H) Growth of MCF7-CK1δ and MCF7-GFP cells 4 days after infection with β-catenin shRNA lentiviruses (n=3, Left to right; *, p=0.0006; , p=0.004, **, p=0.001). Right panel, immunoblot showing CK1δ overexpression and knockdown of β-catenin.

FIG. 6 | CK1δ is a driver of Wnt/β-catenin signaling in vivo. (A) Expression of nuclear and cytoplasmic β-catenin, and (B) the indicated mRNAs, in MDA-MB-231 tumors from mice treated with 20 mg/kg SR-3029 vs. vehicle daily for 7 days (n=4; *, p=0.05; , p=0.01; *, p=0.001). (C) Effects of SR-3029 on tumor Cyclin-D protein expression at day 7. Right panel is quantification (n=3; **, p=0.01). (D) Frequency of CSNK1D copy number amplifications (TCGA) in renal papillary cell carcinoma (renal papillary) and bladder cancer tumors (TCGA). (E) Correlation of CSNK1D DNA copy number and CK1δ expression in renal papillary cell carcinoma (n=172) and bladder cancer (n=220). (F) −log$_{10}$ p-values showing significant overlap between Wnt/β-catenin pathway genes and CK1δ signature lists (p<0.05, fold change >1.5) for indicated cancer types (red line is threshold of significance, p=0.05).

DETAILED DESCRIPTION

Identification of specific drivers of human cancer is required to instruct the development of targeted therapeutics. Here we demonstrate that CSNK1D is amplified and/or overexpressed in human breast tumors and that CK1δ is an unexploited vulnerability of human breast cancer subtypes overexpressing this kinase. Specifically, selective knockdown of CK1δ, or treatment with an in-house, highly selective and potent CK1δ inhibitor, triggers apoptosis of CK1δ-expressing breast tumor cells ex vivo, potent tumor regression in orthotopic models of triple negative breast cancer, including patient derived xenografts, and tumor growth inhibition in HER2+ breast cancer models. Notably, we show that Wnt/β-catenin signaling is a hallmark of human tumors overexpressing CK1δ, that disabling CK1δ blocks nuclear accumulation of β-catenin and T-cell factor transcriptional activity, and that constitutively active β-catenin overrides the effects of inhibition or silencing of CK1δ. Thus, CK1δ inhibition represents a promising strategy for targeted treatment in human breast cancer having Wnt/β-catenin involvement.

We sought to assess the functional role and potential clinical relevance of CK1δ and/or CK1ε as exploitable vulnerabilities in breast cancer. Herein we establish that CK1δ is a promising target for breast cancer therapeutics, and demonstrate the efficacy of an in-house, selective and potent small molecule inhibitor that is effective against breast cancer subtypes overexpressing CK1δ. Further, we demonstrate that the gene encoding CK1δ, CSNK1D, is frequently amplified and/or overexpressed in a subset of human breast cancers, across each of the major breast cancer subtypes, and that knockdown or inhibition of CK1δ provokes breast tumor regression in patient derived xenograft and breast cancer cell line orthotopic xenograft models of TNBC and HER2+ breast cancer. Notably, our mechanistic studies have established that CK1δ activity is a critical driver of Wnt/β-catenin pathway activation in breast cancers, a molecular phenotype known to associate with poor prognosis in breast cancer patients.

Our results are discussed in greater detail below. Our invention provides a method of inhibiting casein kinase 1δ (CK1δ), and consequently, a method of treating breast cancer, comprising contacting the CK1δ, e.g., in the tissue of a living patient, with an effective amount of a compound of formula (I), or more specifically a compound of formula SR-3029, the structures of which are shown above.

CSNK1D is Amplified and/or Overexpressed in a Subset of Human Breast Cancers

Figure 1:
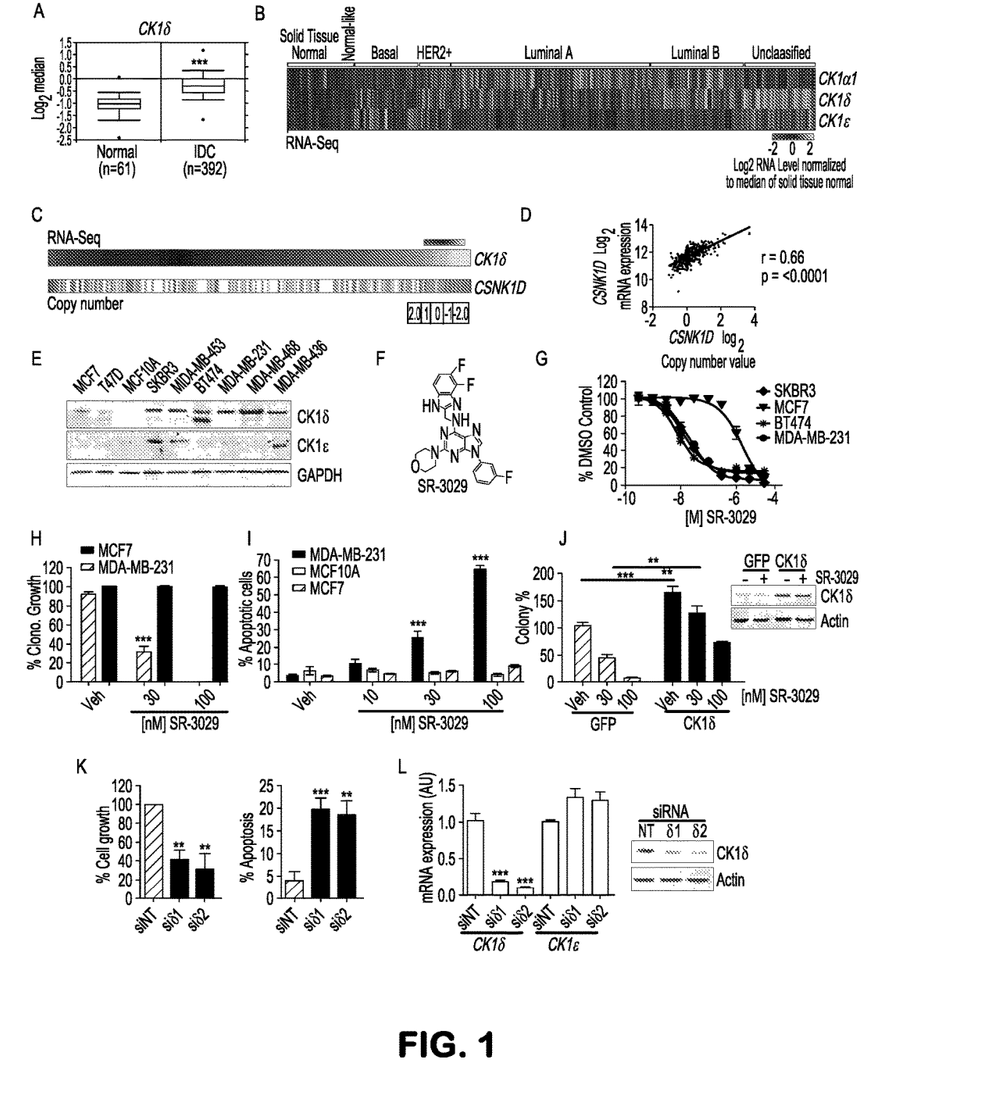

To assess the involvement of CK1δ and CK1ε in human breast cancer we examined the expression of each isoform in human breast tumor specimens compared to normal mammary tissue. Analysis of the cancer genome atlas (TCGA) datasets revealed highly elevated expression of CK1δ (CSNK1D) in invasive breast carcinomas (FIG. 1A), and in an independent dataset. Assessment of CK1 isoform expression across the four major breast cancer subtypes (Pam50 intrinsic classifications) (18) revealed that CK1δ is widely overexpressed within a subset of tumors across each major class (FIG. 1B). In contrast, CK1ε expression is more restricted to the basal-like subclass (FIG. 1B) and is not associated with invasive breast carcinoma. Strikingly, gene copy number analysis (TCGA) revealed amplification (high and low level) of 17q25.3 involving the CSNK1D locus in over a third (36%) of human breast tumors, with higher frequencies of amplification in the luminal B and basal-like classes. In contrast, the CSNK1E locus was not amplified in breast cancer (data not shown). Notably, increased CSNK1D copy number significantly correlates with the expression of CK1δ transcripts (p-value<0.0001) with increased correlation observed within the HER2+, Basal-Like and Luminal B subtypes compared to the Luminal A tumors (FIGS. 1C and D). Consistent with these findings, immunohistochemical analyses confirm overexpression of CK1δ in human breast tumor specimens versus normal breast tissue and CK1δ was overexpressed across a panel of human breast cancer cell lines (FIG. 1E). By contrast, high CK1ε expression was detected in only 3 of the breast cancer cell lines analyzed (FIG. 1E) and expression of both CK1 isoforms was low in immortal human MCF10A breast epithelial cells as well as in the MCF7 and T47D ER+ breast cancer cells.

A Potent, Highly Specific CK1δ/CK1ε Inhibitor Selectively Inhibits Breast Cancer Cell Growth and Survival We recently reported initial structure activity relationships of a series of small molecule dual inhibitors of CK1δ and CK1ε (16). For example, SR-3029 (FIG. 1F), is an ATP competitive inhibitor with exceptional potency and selectivity, and therefore constitutes an ideal small molecule probe of CK1δ/CK1ε biology. Cell proliferation assays revealed that breast cancer cell types overexpressing CK1δ are extremely sensitive to CK1δ/CK1ε inhibition with $EC_{50}$'s in the low nanomolar range (5-70 nM). In contrast, MCF7 and T47D breast cancer cells and the MCF10A cell line, which all expressed low levels of CK1δ, were 2-3 orders of magnitude less sensitive to SR-3029 (FIG. 1G). This selectivity for breast cancer cells overexpressing CK1δ was confirmed in clonogenic growth assays where SR-3029 completely blocked clonogenic growth and survival of MDA-MB-231 cells, but had no effect on the colony forming capacity of MCF7 breast cancer cells (FIG. 1H). Finally, FACS analysis established that SR-3029 treatment selectively triggered rapid apoptosis of CK1δ overexpressing breast cancer cells (FIG. 1I).

We confirmed that the anti-cancer effects of SR-3029 were due to on-target inhibition of CK1δ and/or CK1ε. First, forced overexpression of CK1δ augmented the clonogenic growth of MDA-MB-231 TNBC cells versus GFP-expressing controls, and was sufficient to rescue the growth inhibitory effects of SR-3029 (FIG. 1J). Second, simultaneous knockdown of CK1δ and CK1ε, or silencing of CK1δ alone, triggered apoptosis and impaired the growth of MDA-MB-231 cells (FIG. 1K, L). This effect was specific, as expression of siRNA resistant CK1δ cDNA effectively rescued the growth inhibitory effects of CK1δ silencing. Notably, knockdown of CK1ε alone had no effect on MDA-MB-231 cell growth and survival. Finally, we investigated if there were any potential off target effects. SR-3029 inhibits only 1% of the kinome and has a weaker affinity for only three kinases in addition to CK1δ and CK1ε (CDK4, MYLK4 and FLT3) (16). Of these, only FLT3 is a common (and weak) off-target of SR-3029 and its close analogues SR-2890 and SR-1277, which all show similar anti-proliferative activities against human cancer cells (16), including MDA-MB-231 TNBC cells. In contrast, these cells are insensitive to AC220, a low nanomolar inhibitor of FLT3 and FLT3 mutants. Collectively, these findings establish CK1δ as a biologically relevant target of SR-3029 that is required for the growth and survival of certain breast cancer cells.

Silencing or Inhibition of CK1δ Provokes Potent Anti-Tumor Effects In Vivo

Figure 2:
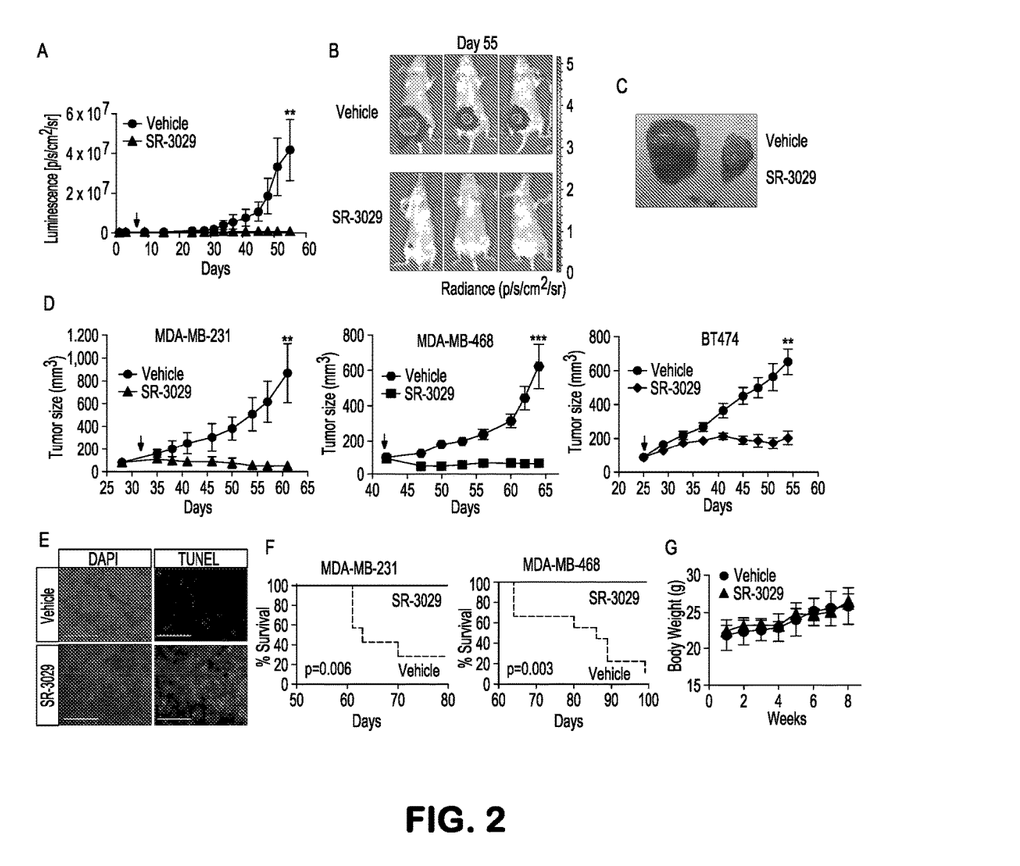

SR-3029 exhibits pharmacokinetic properties amenable for in vivo studies (16). Accordingly, we tested the efficacy of SR-3029 in preclinical tumor models. MDA-MB-231 TNBC cells engineered to express firefly luciferase were engrafted into the mammary fat pads of immunodeficient nude mice and seven days later treatment began. As a single agent SR-3029 (20 mg/kg daily i.p.) markedly impaired tumor growth (FIG. 2A, B). Indeed, only 2 recipients subjected to SR-3029 therapy developed tumors, and these were strikingly small in size compared to those that arose in vehicle treated mice (FIG. 2B, C). Next, orthotopic MDA-MB-231, MDA-MB-468 (TNBC), SKBR3 and BT474 (HER2+) tumor xenografts were allowed to reach an average size of 100-mm³ prior to treatment. Daily i.p. administration of SR-3029 (20 mg/kg) provoked marked tumor growth inhibition in all xenograft models (FIG. 2D). Notably, regression of aggressive MDA-MB-231 tumors was associated with fulminant apoptosis (FIG. 2E) and a significantly prolonged lifespan (FIG. 2F). Moreover, analysis of body weight, blood chemistry and tissue integrity by histochemistry revealed that long-term daily dosing with SR-3029 (48 days) is well tolerated, with no overt toxicity (FIG. 2G).

Figure 3:
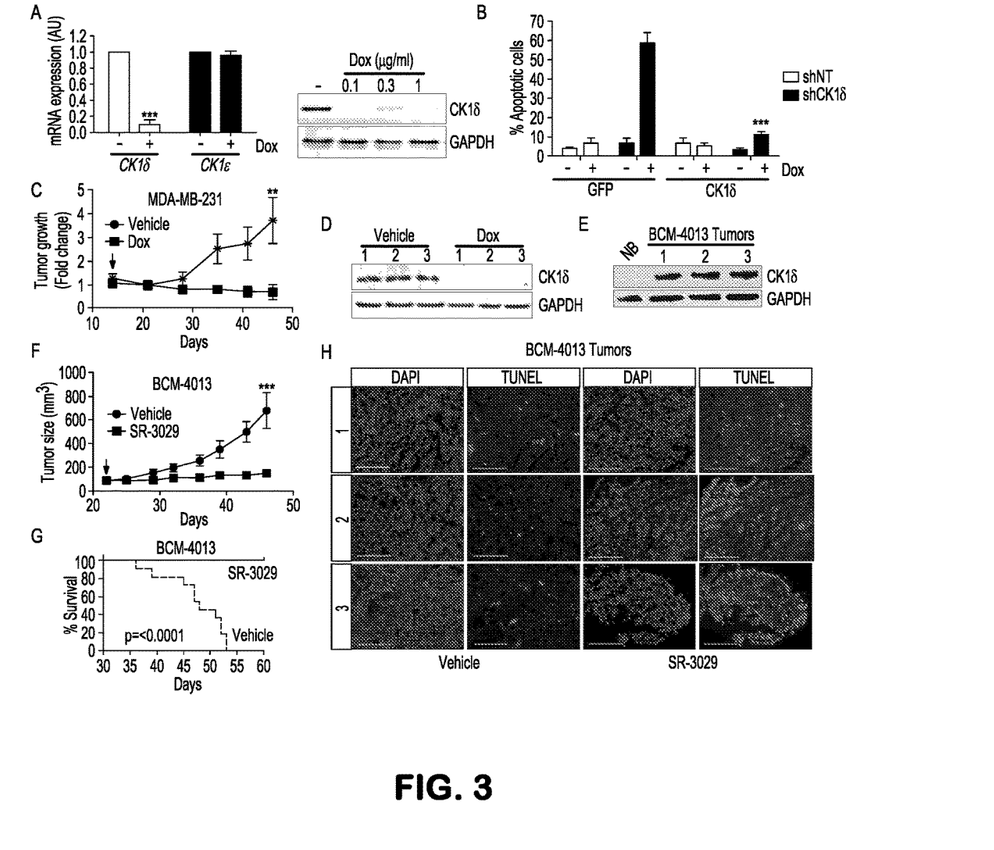

To confirm the effect of CK1δ inhibition on impaired tumor growth in vivo, MDA-MB-231 cells were engineered to stably express a doxycycline (Dox)-inducible shRNA-directed against CK1δ (MDA-MB-231-shCK1δ). Treatment of these cells with Dox ex vivo led to efficient and selective knockdown of CK1δ and rapid apoptosis/cell growth inhibition, and this effect was rescued by exogenous expression of shRNA resistant CK1δ (FIG. 3A, B). Following establishment of orthotopic xenografts of MDA-MB-231-shCK1δ tumors (>100-mm³), administration of Dox and inducible knockdown of CK1δ led to a marked suppression of tumor growth, consistent with results obtained with SR-3029 (FIG. 3C, D). We also assessed the effects of SR-3029 on growth of a primary-patient derived xenograft (PDX) model, BCM-4013; an aggressive basal-like invasive ductal carcinoma with limited response to treatment with dasatinib and docetaxel. Notably, histological and molecular profiling of this stably passaged PDX recapitulates many features of the primary tumor including response to treatment (19).

Following expansion of the BCM-4013 PDX model in vivo, orthotopic tumors were established, tested for expression of CK1δ (FIG. 3E) and efficacy studies performed. In accord with cell line models, administration of SR-3029 (20 mg/kg daily i.p.) significantly inhibited the growth of these PDX tumors and triggered tumor cell apoptosis (FIG. 3F-H) (p=0.0002). These studies establish that CK1δ expression predicts sensitivity to SR-3029 and indicate that CK1δ is an efficacious breast cancer target with potential relevance to human disease.

Wnt/β-catenin Signaling is a Hallmark of CK1δ-Expressing Breast Cancers

Figure 4:
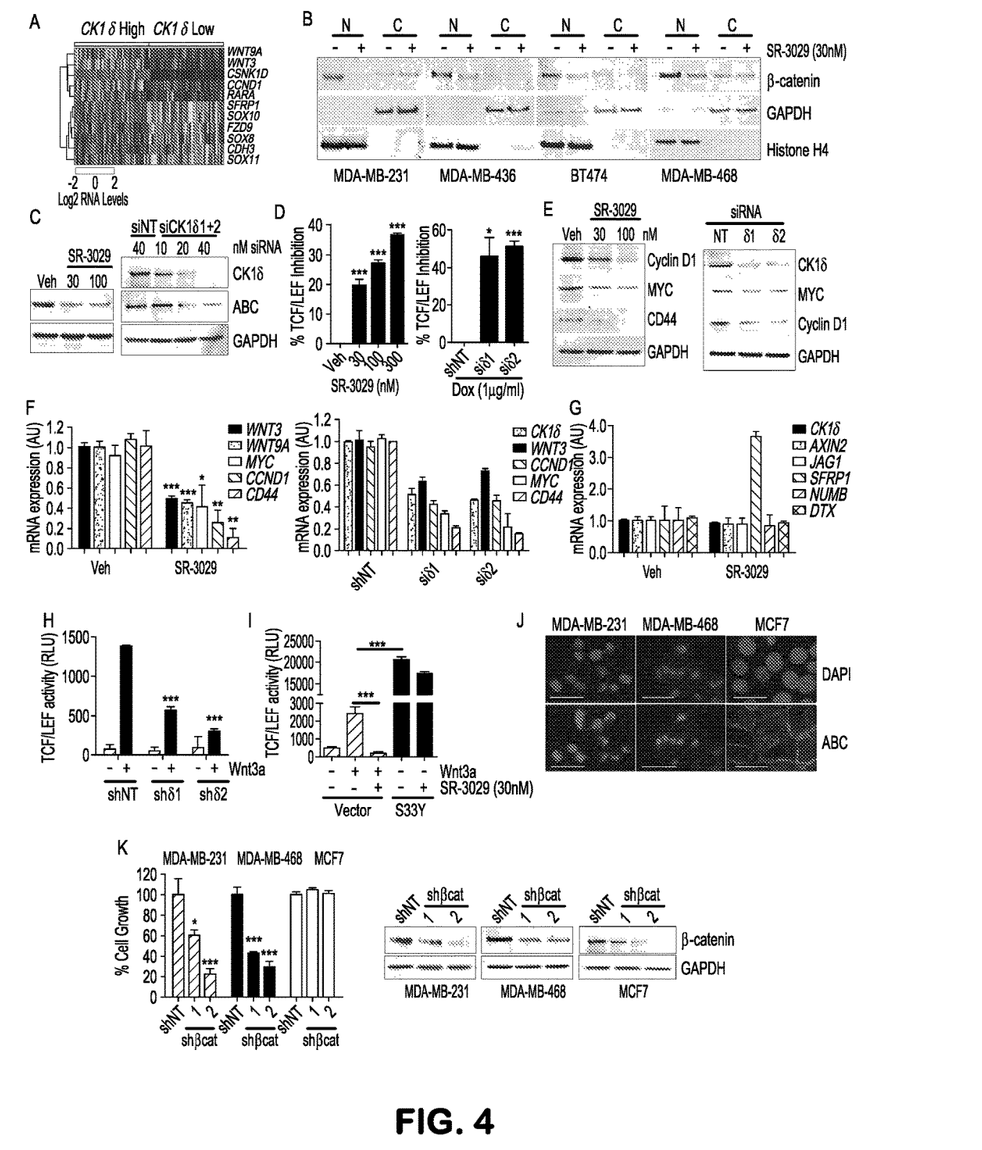

To define pathways regulated by CK1δ in human breast cancer and to identify potential biomarkers for CK1δ inhibition, TCGA patient tumor datasets were analyzed for gene signatures associated with CK1δ overexpression. 612 genes were identified whose expression significantly correlated with CK1δ expression (fold change >2, p-value <0.05), and Ingenuity Pathway Analysis (IPA) identified significant overlap with genes of the canonical Wnt pathway, including Wnt/β-catenin targets (CCND1), Wnt pathway components (FZD9) and endogenous modulators of the pathway (WNT3, WNT9A and SFRP1) (Secreted frizzled-related protein 1) (FIG. 4A).

Importantly, while activated Wnt/β-catenin signaling is associated with poor clinical outcome, pathway-activating mutations typical of other cancer types are rare in breast cancer (20, 21). These findings suggested the hypothesis that CK1δ is an important activator of the Wnt pathway in human breast tumorigenesis and that genes regulated by this pathway could potentially serve as biomarkers required for further preclinical and clinical development of CK1δ inhibitors.

The role of CK1δ and CK1ε in development and disease has been attributed to both Wnt dependent and independent roles (10, 15, 22, 23). Moreover, the requirement for CK1δ/CK1ε in activation of the canonical Wnt/β-catenin pathway is controversial, with both cell type and context specificities (13, 22). We therefore assessed the effects of CK1δ inhibition on β-catenin activity in CK1δ-expressing breast cancer cells. Activation of Wnt signaling results in the stabilization and nuclear translocation of β-catenin, which together with TCF/LEF transcription factors induces the expression of downstream target genes associated with breast cancer tumorigenesis (24-26). Treatment of (CK1δ overexpressing) MDA-MB-231, MDA-MB-436, MDA-MB-468 and BT474 breast cancer cells with SR-3029 markedly reduced expression of the active, nuclear pool of β-catenin (FIG. 4B). Further, CK1δ knockdown or SR-3029 treatment led to a reduction in the unphosphorylated, active form of β-catenin (ABC, FIG. 4C) and markedly reduced endogenous β-catenin/TCF transcriptional activity, as measured in MDA-MB-231 cells stably expressing a TCF-dependent luciferase reporter (FIG. 4D). Accordingly, selective knockdown of CK1δ or inhibition by SR-3029 repressed the expression of endogenous β-catenin/TCF target genes, including CCND1, MYC, CD44, as well as WNT3 and WNT9A, which were all associated with CK1δ expression in human tumors (FIG. 4E, F). Moreover, SR-3029 treatment also resulted in a marked increase in the expression of the endogenous Wnt antagonist SFRP1, yet had no effect on Notch pathway mRNAs (JAG1, NUMB, DTX) (FIG. 4G), an additional pathway strongly implicated in breast cancer pathogenesis (27).

To test if inhibition of CK1δ/CK1ε is sufficient to switch off canonical Wnt signaling in response to Wnt ligands, we generated HEK293T cells stably expressing a TCF-dependent luciferase reporter. As predicted, Wnt-3a-directed induction of the TCF reporter was abolished by treatment with SR-3029 or CK1δ knockdown (FIGS. 4H and I). Further, forced expression of a constitutively active (nuclear) mutant of β-catenin (S33Y) (28) increased TCF reporter activity and this was refractory to the inhibitory effects of SR-3029 (FIG. 4I). Thus, inhibition of CK1δ is sufficient to block activated β-catenin signaling in human breast cancer cells and Wnt-inducible activation of the pathway through canonical signaling.

Figure 5:
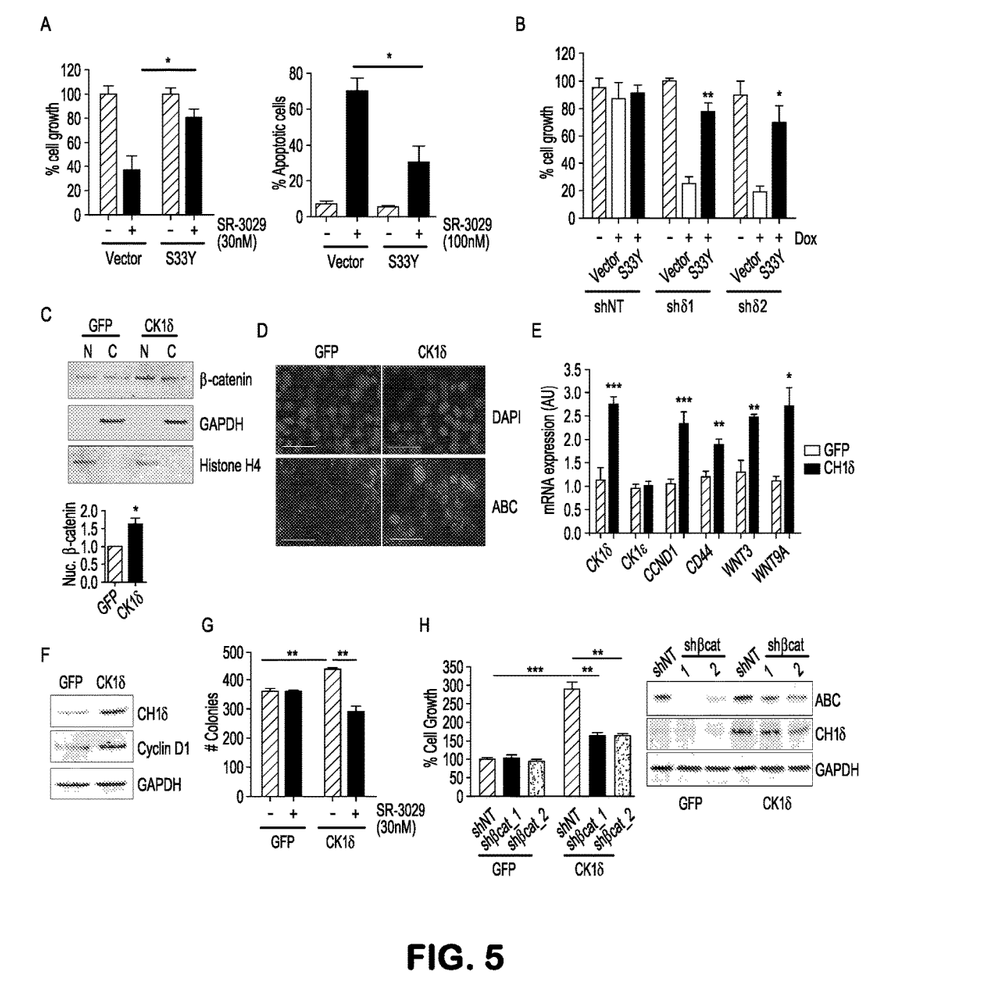

To assess the consequence of impaired Wnt/β-catenin signaling on the tumorigenic growth of human breast cancer cell subtypes that are sensitive to CK1δ inhibition, we expressed β-catenin shRNAs in MDA-MB-231 and MDA-MB-468 cells. Each of these cell types expressed high levels of nuclear β-catenin (FIG. 4J) and were dependent on β-catenin for sustained cell growth and survival (FIG. 4K). Conversely, MCF7 cells, which express little-to-no nuclear β-catenin, were insensitive to β-catenin knockdown, consistent with their low expression of CK1δ and relative insensitivity to SR-3029 (FIG. 4K). To more directly assess the role of impaired β-catenin signaling in the anti-tumor activity of targeting CK1δ, we utilized two constitutively active β-catenin mutants. Forced expression of β-catenin-S33Y, or the NH$_2$-terminal constitutively active mutant (β-catenin N90) was sufficient to rescue the growth inhibitory and apoptotic effects of either SR-3029 or CK1δ knockdown in MDA-MB-231 cells (FIG. 5A, B). Thus, CK1δ controls β-catenin activity, which is necessary for breast cancer cell growth and survival.

MCF7 ER+ breast cancer cells express low levels of CK1δ (FIG. 1E), have reduced expression of active (nuclear) β-catenin versus MDA-MB-231 cells, are refractory to SR-3029 (FIG. 1G) and have limited tumorigenic potential versus other human breast cancer cells (29-31). Notably, MCF7 cells engineered to overexpress CK1δ displayed increased expression of nuclear D-catenin (FIG. 5C, D) and downstream Wnt target genes, including CCND1, CD44, WNT3 and WNT79A (FIG. 5E, F). Further, forced overexpression of CK1δ potentiates the clonogenic growth of MCF7 cells and sensitizes them to SR-3029 in both short-term and long-term growth assays (FIG. 5G). Notably, knockdown of β-catenin was sufficient to impair exogenous CK1δ-driven MCF7 cell growth (FIG. 5H), confirming a critical mechanistic role for the Wnt/β-catenin pathway in the growth promoting activity of CK1δ.

Figure 6:
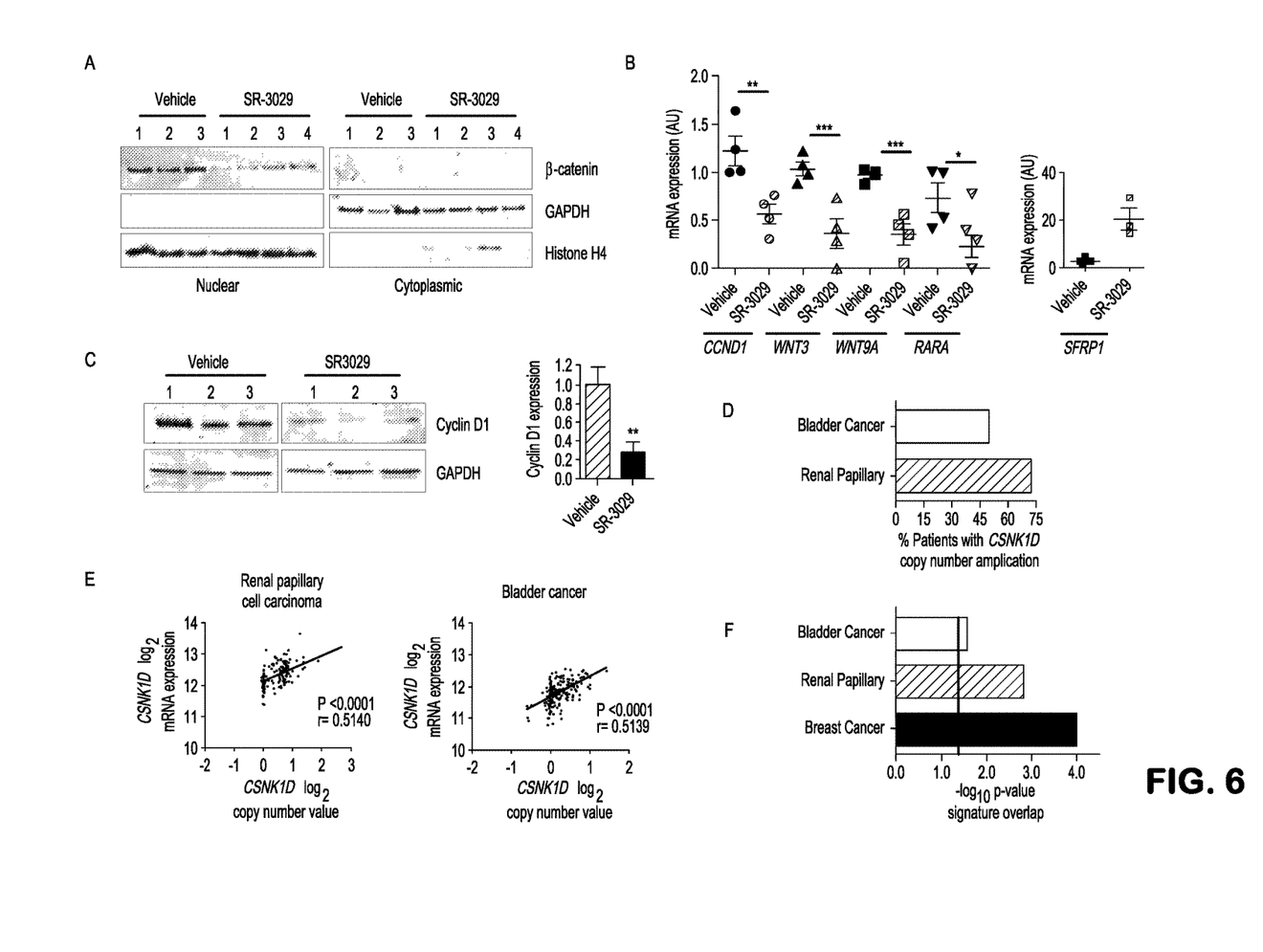

To assess if CK1δ inhibition impairs Wnt/β-catenin signaling in vivo and if modulation of this pathway represent a predictive biomarker, MDA-MB-231 tumors isolated from mice treated for 7 days with 20 mg/kg SR-3029, or vehicle (once daily, i.p. administration) were analyzed for markers of activated β-catenin signaling. Expression of nuclear β-catenin was markedly reduced in tumors derived from SR-3029 treated mice compared to vehicle treated controls (FIG. 6A), and this was associated with decreases in CCND1, WNT3, WNT9A and RARA mRNA transcripts, as well as with a marked increase in expression of SFRP1 transcripts (FIG. 6B). Moreover, down-regulation of CCND1 was observed at the protein level in tumors derived from SR-3029 treated mice as well as in those that had undergone Dox-inducible silencing of CK1δ (FIG. 6C). Finally, as Wnt/β-catenin signaling is known to play a key role in the homeostasis of regenerating tissues, the effects of long-term SR-3029 treatment on the integrity of the small intestine was assessed. Notably, H&E staining revealed no gross morphological defects and TUNEL staining failed to detect evidence of apoptosis, in contrast to that observed in corresponding tumors (FIG. 2E).

Collectively these findings established a link between activation of a CK1δ-to-β-catenin pathway and sensitivity to SR-3029, and suggested that features of this pathway would define tumors that will respond to this targeted therapy. Notably, analyses of additional TCGA cancer datasets revealed CSNK1D copy number amplifications (high and low) in over 70% of patients with papillary renal cell carcinoma and in nearly 50% of patients with bladder cancer, and gene amplification in these tumors also correlated with increased CK1δ expression (FIG. 6D, E). Notably, there was a significant overlap between the CK1δ gene signature list and Wnt pathway genes in both cancer types (CK1δ high vs. CK1δ low, p<0.05, fold change 1.5), (FIG. 6F). Thus, the CK1δ-to-β-catenin signaling circuit may be an unexploited vulnerability across a spectrum of human malignancies.

Identification of specific drivers of human breast cancer has instructed the development of targeted therapies such as trastuzumab for the treatment for HER2 amplified breast cancers and hormonal therapies for the treatment of ER+ breast cancers, and these targeted agents have improved the survival and clinical management of these diseases (32). In contrast, patients with relapsed disease and those with TNBC lack targeted therapies, and represent an urgent unmet clinical need. The data presented herein implicates CK1δ as a highly attractive therapeutic target with potential benefit for HER2+ and TNBC breast cancer patients aberrantly expressing CK1δ.

Heretofore, the role(s) of CK1δ in human cancer have been poorly understood and prior small molecule modulators of CK1δ have lacked either the potency and/or selectivity required to validate CK1δ as an anticancer target (9, 13-15, 33). For example, the probe molecule IC261 used in several studies has subsequently been shown to act not by inhibition of CK1δ/CK1ε, but rather by blocking tubulin function (13). Moreover, studies with the CK1δ/CK1ε dual inhibitor PF670462 have shown that it lacks anti-cancer activity (13, 14), and that this is likely due to important off-target activity against multiple kinases, including several having pro-apoptotic activity (16). In contrast, our small molecule inhibitor (SR-3029) is highly selective, potent (16) and efficacious in multiple preclinical models of human breast cancer. Further, our findings demonstrate that overexpression of CK1δ predicts sensitivity to SR-3029 in cell-based models of the breast cancer, suggesting that dependence on CK1δ is cell type and context specific.

Overexpression of CK1δ, which is widespread across each of the four major breast cancer subtypes, may thus identify tumors that will respond to this targeted treatment strategy. Further study across a broader spectrum of patient-derived tumor samples is needed to fully investigate this hypothesis.

Gain- and loss-of-function mutations in positive (β-catenin) and negative (APC, AXIN1, etc.) regulatory components of the Wnt pathway are prevalent at a high frequency in human cancers (reviewed by (34)). In contrast, while aberrant activation of the Wnt pathway is frequent in breast cancer, (21, 35, 36) mutations in Wnt pathway components in these malignancies are rare (20, 21, 37). Here we have shown that CK1δ-to-β-catenin signaling is activated in a subset of human breast cancers, where silencing or pharmacological inhibition of CK1δ is sufficient to disable β-catenin activity and provoke breast cancer cell apoptosis. Our findings thus implicate CK1δ as a key target kinase that can be exploited (for instance by SR-3029) to disable aberrant Wnt/β-catenin signaling that is manifest in several breast cancer subtypes. Previous reports have described several pathways where CK1δ plays an important role (23, 33). Thus, while the anti-breast cancer activity of SR-3029 clearly targets Wnt/β-catenin signaling, additional effectors could contribute to its substantial anti-tumor activity in vivo.

Collectively, the findings presented herein identify CK1δ as an efficacious therapeutic target with great potential for clinical relevance in a select subset of cancers, including but not exclusively breast cancer, where CK1δ is: (i) activated via amplification and/or overexpression; (ii) a necessary driver of β-catenin activity in these tumor subtypes; and (iii) necessary for the growth and survival of cell and preclinical models of human breast cancer.

Accordingly, in various embodiments, the invention can provide a method of inhibiting casein kinase 1δ (CK1δ), comprising contacting the CK1δ with an effective amount or concentration of a compound of formula (I)

wherein
each R is independently selected hydrogen or $(C_1-C_6)$ alkyl, or two R groups bonded to a nitrogen atom together with the nitrogen atom can form a 5-7 membered heterocyclyl optionally further comprising 1 or 2 heteroatoms selected from the group consisting of O, S, and NR', wherein R' is hydrogen or $(C_1-C_6)$alkyl;

Ar$^1$ is an aryl or a 5-membered or 6-membered heteroaryl, which is unsubstituted or is substituted with 1-3 independently selected halo, $(C_1-C_6)$alkyl, $(C_1-C_6)$fluoroalkyl, $(C_1-C_6)$alkoxyl, cyano, nitro, C(=O)NR$_2$, OC(=O)NR$_2$, N(R)C(=O)OR, N(R)C(=O)R, or C(=O)OR;

Het$^1$ is a monocyclic or bicyclic heteroaryl, which is unsubstituted or is substituted with 1-3 independently selected halo, $(C_1-C_6)$alkyl, $(C_1-C_6)$fluoroalkyl, $(C_1-C_6)$alkoxyl, cyano, nitro, C(=O)NR$_2$, OC(=O)NR$_2$, N(R)C(=O)OR, N(R)C(=O)R, or C(=O)OR;

or a pharmaceutically acceptable salt thereof.

The invention further provides, in various embodiments, a method of treating cancer, comprising administering to a patient afflicted therewith an effective dose of a compound of formula (I)

wherein
each R is independently selected hydrogen or $(C_1-C_6)$ alkyl, or two R groups bonded to a nitrogen atom together with the nitrogen atom can form a 5-7 membered heterocyclyl optionally further comprising 1 or 2 heteroatoms selected from the group consisting of O, S, and NR', wherein R' is hydrogen or $(C_1-C_6)$alkyl;

Ar$^1$ is an aryl or a 5-membered or 6-membered heteroaryl, which is unsubstituted or is substituted with 1-3 independently selected halo, $(C_1-C_6)$alkyl, $(C_1-C_6)$fluoroalkyl, $(C_1-C_6)$alkoxyl, cyano, nitro, C(=O)NR, OC(=O)NR$_2$, N(R)C(=O)OR, N(R)C(=O)R, or C(=O)OR;

Het$^1$ is a monocyclic or bicyclic heteroaryl, which is unsubstituted or is substituted with 1-3 independently selected halo, $(C_1-C_6)$alkyl, $(C_1-C_6)$fluoroalkyl, $(C_1-C_6)$alkoxyl, cyano, nitro, C(O)NR$_2$, OC(=O)NR$_2$, N(R)C(=O)OR, N(R)C(=O)R, or C(=O)OR; or a pharmaceutically acceptable salt thereof.

For example, the compound of formula (I) can be or a pharmaceutically acceptable salt thereof.

The cancer that can be treated with an effective amount of a compound of formula (I) can be a cancer with upregulated expression levels of both CK1δ and β-catenin. For example, the cancer can be breast cancer, melanoma, glioblastoma, medulloblastoma, renal, bladder or colon cancer, or can be a cancer that metastasizes to the brain, lung, or bone provided that both elevated CK1δ and β-catenin dependence are involved in those metastatic diseases. For example, the breast cancer can be of the triple negative subclass of breast cancers (TNBC) or is an HER+ breast cancer.

Accordingly, the invention can provide a compound of formula (I) of claim 1 for treatment of cancer, such as wherein the compound is SR-3029, or a pharmaceutically acceptable salt thereof.

The cancer that can be treated with an effective dose of a compound of formula (I) can be a breast cancer, melanoma, glioblastoma, medulloblastoma, renal, bladder or colon cancer, or can be a cancer that metastasizes to the brain, lung, or bone provided that both elevated CK1δ and β-catenin dependence are involved in those metastatic diseases. For example, the cancer can be a breast cancer of the triple negative subclass of breast cancers (TNBC) or can be an HER+ breast cancer.

The invention further discloses that cancers particularly susceptible to treatment with CK1δ inhibitors are those cancers with upregulated expression levels of both CK1δ and β-catenin. Accordingly, the invention provides, in various embodiments, a method of identifying an anticancer drug effective for treatment of a cancer in a patient, comprising determining a level of CK1δ and a level of β-catenin in the patient and selecting a CK1δ inhibitor as the anticancer drug if both the levels are elevated. Further, the invention can provide a method of treating in a patient a breast cancer, a melanoma, a glioblastoma, a medulloblastoma, or a renal, bladder or colon cancer, or a cancer that metastasizes to the brain, lung, or bone, comprising determining if elevated CK1δ and β-catenin levels are present in the patient, and if both levels are elevated, selecting a CK1δ inhibitor for a treatment regimen. The level of CK1δ and the level of β-catenin can be determined using ordinary skill and knowledge in the art in conjunction with the disclosed subject matter herein. A level of CK1δ or β-catenin in a patient is considered to be "elevated" if its concentration in body tissue is statistically significantly higher than average levels in comparable patients.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents, or provides prophylaxis for, the disorder or condition. In particular, a "therapeutically effective amount" refers to an amount that is effective, at dosages and for periods of time necessary, to achieve the desired therapeutic result. A therapeutically effective amount is also one in which any toxic or detrimental effects of compounds of the invention are outweighed by the therapeutically beneficial effects.

The expression "effective amount", when used to describe therapy to an individual suffering from a disorder, refers to the quantity or concentration of a compound of the invention that is effective to inhibit or otherwise act on CK1δ in the individual's tissues wherein CK1δ is involved in the disorder, such as breast cancer, wherein such inhibition or other action occurs to an extent sufficient to produce a beneficial therapeutic effect.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used. Compounds useful in practice of the invention can be prepared according to literature procedures in conjunction with ordinary knowledge and skill in organic synthesis.

All single enantiomer, diastereomeric, and racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

When a number of carbon atoms in a group, e.g., an alkyl, alkenyl, alkynyl, cycloalkyl, aryl, etc., is specified as a range, each individual integral number representing the number of carbon atoms is intended. For example, recitation of a $(C_1-C_4)$alkyl group indicates that the alkyl group can be any of methyl, ethyl, propyl, isopropyl, butyl, sec-butyl, isobutyl, or tert-butyl. It is understood that a specification of a number of carbon atoms must be an integer.

In general, "substituted" refers to an organic group as defined herein in which one or more bonds to a hydrogen atom contained therein are replaced by one or more bonds to a non-hydrogen atom such as, but not limited to, a halogen (e.g., F, Cl, Br, or I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, nitroso groups, N-oxides, hydrazides, azides, and enamines; and other heteroatoms in various other groups. Non-limiting examples of substituents that can be bonded to a substituted carbon (or other) atom include F, Cl, Br, I, OR, CN, NO, $NO_2$, $ONO_2$, azido, $CF_3$, $OCF_3$, R, O (oxo), S (thiono), methylenedioxy, ethylenedioxy, $N(R)_2$, SR, SOR, $SO_2R$, $SO_2N(R)_2$, $SO_3R$, C(O)R, C(O)C(O)R, C(O)$CH_2$C(O)R, C(S)R, C(O)OR, OC(O)R, C(O)$N(R)_2$, OC(O)$N(R)_2$, C(S)

N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein R can be hydrogen or a carbon-based moiety, and wherein the carbon-based moiety can itself be further substituted; for example, R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl can be further independently mono- or multi-substituted with some or all of the above-listed functional groups, or with other functional groups; or wherein two R groups bonded to a nitrogen atom or to adjacent nitrogen atoms can together with the nitrogen atom or atoms form a heterocyclyl, which can be further mono- or independently multi-substituted with some or all of the above-listed functional groups, or with other functional groups.

In various embodiments, a substituent can be halo, nitro, cyano, OR, NR$_2$, or R, or is C(O)OR, C(O)NR$_2$, OC(O)OR, OC(O)NR$_2$, N(R)C(O)OR, N(R)C(O)NR$_2$ or thio/thiono analogs thereof. By "thio/thiono analogs thereof", with respect to a group containing an O, is meant that any or all O atoms in the group can be replaced by an S atom; e.g., for group C(O)OR, a "thio/thiono analog thereof" includes C(S)OR, C(O)SR, and C(S)SR; e.g., for group OC(O)NR$_2$, a "thio/thiono analog thereof" includes SC(O)NR$_2$, OC(S)NR$_2$, and SC(S)NR$_2$; and so forth.

In various embodiments, a substituent can be any of halo, (C1-C6)alkyl, (C1-C6)alkoxy, (C1-C6)haloalkyl, hydroxy(C1-C6)alkyl, alkoxy(C1-C6)alkyl, (C1-C6)alkanoyl, (C1-C6)alkanoyloxy, cyano, nitro, azido, R$_2$N, R$_2$NC(O), R$_2$NC(O)O, R$_2$NC(O)NR, (C1-C6)alkenyl, (C1-C6)alkynyl, (C6-C10)aryl, (C6-C10)aryloxy, (C6-C10)aroyl, (C6-C10)aryl(C1-C6)alkyl, (C6-C10)aryl(C1-C6)alkoxy, (C6-C10)aryloxy(C1-C6)alkyl, (C6-C10)aryloxy(C1-C6)alkoxy, (3- to 9-membered)heterocyclyl, (3- to 9-membered)heterocyclyl(C1-C6)alkyl, (3- to 9-membered)heterocyclyl(C1-C6)alkoxy, (5- to 10-membered)heteroaryl, (5- to 10-membered)heteroaryl(C1-C6)alkyl, (5- to 10-membered)heteroaryl(C1-C6)alkoxy, or (5- to 10-membered)heteroaroyl.

Alkyl groups include straight chain and branched carbon-based groups having from 1 to about 20 carbon atoms, and typically from 1 to 12 carbons or, in some embodiments, from 1 to 8 carbon atoms, or from 1 to 4 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl.

The terms "halo" or "halogen" or "halide" by themselves or as part of another substituent mean, unless otherwise stated, a fluorine, chlorine, bromine, or iodine atom, preferably, fluorine, chlorine, or bromine.

The term "fluoroalkyl" includes mono- and poly-fluoro alkyl groups; examples include CF$_3$, C$_2$F$_5$, and the like.

The term "alkoxy" or "alkoxyl" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, and the like. Examples of branched alkoxy include but are not limited to isopropoxy, sec-butoxy, tert-butoxy, isopentyloxy, isohexyloxy, and the like. Exemplary alkoxy groups include, but are not limited to, alkoxy groups of 1-6 or 2-6 carbon atoms, referred to herein as C$_{1-6}$alkoxy, and C$_{2-6}$alkoxy, respectively. Exemplary alkoxy groups include, but are not limited to methoxy, ethoxy, isopropoxy, etc.

Aryl groups are cyclic aromatic hydrocarbons that do not contain heteroatoms in the ring. An aromatic compound, as is well-known in the art, is a multiply-unsaturated cyclic system that contains 4n+2π electrons where n is an integer. Thus aryl groups include monocyclic and polycyclic ring systems. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Heterocyclyl groups or the term "heterocyclyl" includes aromatic and non-aromatic ring compounds containing 3 or more ring members, of which one or more ring atom is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members.

Heteroaryl groups are heterocyclic aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure, which is a multiply-unsaturated cyclic system that contains 4n+2π electrons wherein n is an integer.

The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention. "Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

It is within ordinary skill to evaluate any compound disclosed and claimed herein for effectiveness in inhibition of CK1δ and in the various cellular assays using the procedures described above or found in the scientific literature. Accordingly, the person of ordinary skill can prepare and evaluate any of the claimed compounds without undue experimentation.

Any compound found to be an effective inhibitor of CK1δ can likewise be tested in animal models and in human clinical studies using the skill and experience of the investigator to guide the selection of dosages and treatment regimens, e.g., for treatment of breast cancer.

Compounds used in the practice of methods of the invention can be prepared using ordinary knowledge and skill of a synthetic organic chemist, based on literature procedures, including those of published PCT application "WEE1 Degradation Inhibitors", by certain of the inventors herein, serial number PCT/US2013/027784, WO2013/130461, the disclosure of which is incorporated by reference herein in its entirety.

EXAMPLES

Study Design

This study was designed to assess the involvement of CK1δ and CK1ε in human breast cancer and to investigate the efficacy of an in-house, highly specific dual CK1δ/CK1ε inhibitor in pre-clinical models of human breast cancer. Five human orthotopic breast xenograft models, pharmacological and genetic studies were used to validate targeting CK1δ in subsets of breast cancer that overexpress this kinase. Power analyses suggested that based on the difference in tumor volume between groups and the standard deviation of tumor volumes within each group for confidence of 90%, an n of at least 7 or greater is required. Our experiments therefore included 7-12 tumor bearing mice per experimental or control (vehicle) cohort with mice randomized prior to treatment to determine random sampling such that the median tumor size between cohorts was the same. All tumors sizes were measured throughout the duration of the experiment and graphed in figures without excluding any samples. For survival analyses, mice were euthanized when moribund, and/or when tumors became ulcerated or reached greater than 1.2 $cm^3$. All cell-based assays were performed in triplicate and repeated at least 3 times.

Xenograft Tumor Models and Bioluminescent Imaging of Mice.

All animal studies are approved by the Scripps Florida IACUC. Stable pools of MDA-MB-231-Luc, MDA-MB-231, MDA-MB-468, SKBR3 or BT474 cells were established by injection of $2 \times 10^6$ cancer cells into the mammary fat pads of 6-week old female athymic nude mice (Charles River Laboratories). Establishment of BCM-4013 patient derived xenografts were as described (19). Briefly, fresh xenograft tumor fragments (~1 $mm^3$) were transplanted into the cleared mammary fat pad of recipient SCID/Bg mice (Charles River Laboratories). Mice were treated with SR-3029 or vehicle (10:10:80, DMSO:Tween-80:Water) at 20 mg/kg daily by i.p. injection. Tumor volumes were measured at the indicated intervals using calipers or by luminescence imaging using the IVIS 100 imager (exposure time, 1-60 sec; binning 8; field of view 15-cm; f/stop 1; open filter) following subcutaneous injection of luciferin (15 mg/ml, Goldbio Technology). Average radiance (p/s/$cm^2$/sr) was determined from tumor region-of-interest (ROI) using Living-Image (Xenogen) analysis software.

Cell Proliferation and Clonogenicity Assays.

Cell proliferation was measured 72 hr after SR-3029 or vehicle treatment using Cell-Titer Glo (Promega) according to the manufacturers' instructions. $EC_{50}$ values were determined using non-linear regression and a four-parameter algorithm (GraphPad Prism5). For clonogenic assays, cells were plated in 6-well dishes in triplicate at a density of 500-1000 cells per well. After overnight incubation, SR-3029 or vehicle (DMSO) was added to media for 72 hr and cells were allowed to grow out for 7-10 days, during which media was changed every 2-3 days in the absence of compound. Colonies were fixed in 4% paraformaldehyde/PBS and stained with 0.5% methylene blue in 50% ethanol for 1 hr at room temperature and de-stained with water. Colonies with greater than 50 cells were counted using a low magnification light microscope.

Reagents, Cell Lines and Transfection.

Unless otherwise stated all chemicals were purchased from Sigma Aldrich. MDA-MB-231, MDA-MB-436, MDA-MB-468, HS578T, BT474, SKBR3, MDA-MB-453, MCF7 and T47D breast cancer cells, and immortal MCF-10A breast epithelial cells, were from the American Type Culture Collection (ATCC). For CK1δ and CK1ε knockdown, siRNA duplexes were prepared according to the manufacturer's instructions (Qiagen) and specific knockdown conditions were optimized using the HiPerfect transfection reagent (Qiagen). A final concentration of 20 nM total siRNA was used to achieve knockdown. FuGene6 (Roche) was used for DNA transfections as per manufacturer's instructions.

Lentiviral Transduction.

Lentiviral vectors expressing CK1δ (Y3989-Lv105-0200, GeneCopoeia), GFP (EGFP-Lv105-0200, GeneCopoeia), luciferase or the TCF reporter 7TFP (Addgene, Roel Nusse) were co-transfected with pPACKH1 packaging plasmids into HEK293T cells to produce lentiviral particles per the manufacturers' recommendations (System Biosciences). To stably express specific shRNAs shRNA oligonucleotides were cloned into the Tet-pLKO-Puro vector using the recommended protocol (38) and lentiviruses were generated using the Mission Packaging System (Sigma). MDA-MB-231 cells were transduced with optimized titers of lentiviruses and infected cells were selected in puromycin (1 μg/ml) or blasticidin (5 μg/ml for luciferase lentivirus) containing medium to expand stably infected pools.

Immunoblotting.

SDS-PAGE gel electrophoresis was performed using NuPAGE 4-12% Bis-Tris gels (Invitrogen) and transferred to PVDF membranes by semi-dry transfer using trans-blot transfer medium (Biorad). Membranes were blocked in Odyssey blocking buffer (LI-COR Biosciences) and incubated overnight at 4° C. with primary antibodies. After repeated washes with TBST (20 mM Tris, pH 7.6, 140 mM NaCl and 0.1% Tween-20) blots were incubated with the appropriate IRDye-conjugated secondary antibody (LI-COR Biosciences) and imaged using the LI-COR Odyssey. Bands were quantified using the Odyssey software (LI-COR Biosciences). The following antibodies were used in this study: CK1δ and Histone H4 (Abcam), CK1ε, c-Myc (9E10), Cyclin-D1 and β-actin (Santa Cruz), β-catenin (Cell Signaling), GAPDH (Millipore) and CD44 (R&D Systems).

Quantitative Real-Time PCR.

Total RNA was obtained using the RNeasy Plus Mini Kit (Qiagen) and 1-2 μg of RNA was reverse transcribed with Superscript III First Strand Synthesis System (Life Technologies). Quantitative PCR was performed using the Power SYBR Green PCR Master Mix (Life Technologies) and the ABI7900HT Fast Real-Time PCR System. Intron-spanning gene-specific primer pairs were designed using the Primer3 algorithm and relative expression values for each gene of interest obtained by normalizing to GAPDH mRNA expression using the $^{\Delta\Delta}C_t$ method.

Immunocytochemistry and H&E Staining.

For apoptotic detection in cryosections tumors and small intestines were fixed in 10% buffered formalin for 2 hr, incubated in 20% sucrose overnight and embedded in OCT. Frozen sections (5 μM) were mounted and stained using the ApopTag Red In Situ Kit according to the manufacturer instructions (CHEMICON). For H&E staining, tissues were fixed in 10% buffered formalin for 48 hr, transferred to 70% ethanol/PBS and embedded in paraffin. Staining was performed on 5 μM sections following deparaffinization (AML Laboratories).

Flow Cytometry.

$2 \times 10^5$ cells seeded in triplicate in 6-well dishes were cultured with SR-3029 or vehicle for 72 hr. Cells were then harvested and stained with Annexin V-FITC and PI using the Annexin V-FITC Apoptosis Detection Kit (BioVision) per the manufacturer's instructions and analyzed using the LSRI II flow cytometer (Becton Dickinson). Staurosporine (Cell Signaling) treated cells (1 μM) were used as positive/compensation controls.

TCF Reporter Assays.

MDA-MB-231 or HEK293 cells stably expressing the TCF luciferase reporter 7TFP (39) were transfected with β-catenin-S33Y or empty vector (pcDNA). After 18 hr cells were seeded onto a 96-well plate at a density of 6000 cells/well. After 24 hr cells were treated with SR-3029 or vehicle and incubated for 6 hr prior to addition of 1 μg/ml recombinant human Wnt3a (R&D Systems) or PBS. After 3 hr, reporter assays were performed using BriteLite Plus (Perkin Elmer), which was added in equal volume directly to the media and luminescence read using a Spectramax plate reader (Molecular Devices).

Bioinformatics Analyses.

The Cancer Genome Atlas (TCGA) Data Retrieval; Breast cancer (BRCA), kidney renal papillary cell carcinoma (KIRC) and bladder cancer (BLCA) gene expression and copy number datasets were downloaded from the TCGA portal (http://tca-data.nci.nih.gov/). For expression profiling, level 3 expression data of 20,475 genes from the RNASeqV2 platform was downloaded.

For gene expression profiling analysis, RNA-Sequencing (RNA-Seq) by Expectation-Maximization (RSEM) normalized count was used to analyze gene-expression estimates for the RNASeqV2 data from TCGA Breast cancer dataset. $Log_2$ normalized counts were imported into GeneSpring GX V12.1 (Agilent Technologies). Baseline transformation was set as the median for all samples for each dataset (919 breast, 228 kidney and 260 bladder cancer samples).

To identify the CK1δ gene signature list, the upper 100 and lower 100 tumor breast tumor samples (CK1δ-high and CK1δ-low groups) or upper and lower quartiles for smaller datasets (kidney and bladder cancer) were defined based on CK1δ (CSNK1D) expression. Out of 20,501 genes, only genes expressing higher than median in at least one sample were filtered for downstream analysis. GeneSpring Volcano Plot function was used to identify differentially expressed genes between the CK1δ-high and CK1δ-low groups. Statistical test parameters were set as follows: selected test, unpaired t-test; p-value computation, Asymptotic, multiple testing correction, Benjamini-Hochberg. Corrected p-value cut-off was set to 0.05 and fold change cut-off was as indicated in the text.

To generate heatmaps, the GeneSpring hierarchical clustering algorithm was used. The similarity measure was set to Pearson centered, and the linkage rule was set to average. Ingenuity Pathway Analysis software (Qiagen) was used to identify canonical pathways having overlap with the CK1δ gene signature in the breast cancer dataset. Fisher's exact test was used for significance (p-value <0.05). For analysis of additional cancer datasets, the list of IPA Wnt/j-catenin signaling genes (172 genes) was imported into GeneSpring and the p-value of overlap with the Ck1δ signature lists calculated using GeneSpring software (probability of overlap formula).

Copy number analysis, TCGA RNA-seq and GISTIC2 thresholded copy number data were ordered based on CSNK1D RNA-Seq expression. To confirm the correlation, a scatter plot was generated in GraphPad Prism 6 based on $log_2$ mRNA expression and $log_2$ copy number values (40). Pearson r and p-value were calculated using GraphPad Prism 6.

Statistical Analysis.

All values in figures are presented as means±SE unless otherwise stated. Survival curves were calculated by using Kaplan-Meier method and differences between the curves were determined by log rank test. Correlation coefficients were calculated using the Pearson test. Detailed information regarding bioinformatics analyses are noted above. All other experiments were analyzed using Student's two-tailed t test in excel or prism where p values ≤0.05 were considered significant.

DOCUMENTS CITED

1. E. A. Rakha, J. S. Reis-Filho, F. Baehner, D. J. Dabbs, T. Decker, V. Eusebi, S. B. Fox, S. Ichihara, J. Jacquemier, S. R. Lakhani, J. Palacios, A. L. Richardson, S. J. Schnitt, F. C. Schmitt, P. H. Tan, G. M. Tse, S. Badve, I. O. Ellis, Breast cancer prognostic classification in the molecular era: the role of histological grade. *Breast Cancer Res* 12, 207 (2010) 10.1186/bcr2607).
2. N. Cancer Genome Atlas, Comprehensive molecular portraits of human breast tumours. *Nature* 490, 61-70 (2012); published online EpubOct 4 (10.1038/nature11412).
3. R. Siegel, J. Ma, Z. Zou, A. Jemal, Cancer statistics, 2014. *CA: a cancer journal for clinicians* 64, 9-29 (2014); published online Epub January-February (10.3322/caac.21208).
4. F. Andre, K. Slimane, T. Bachelot, A. Dunant, M. Namer, A. Barrelier, O. Kabbaj, J. P. Spano, H. Marsiglia, R. Rouzier, S. Delaloge, M. Spielmann, Breast cancer with synchronous metastases: trends in survival during a 14-year period. *Journal of clinical oncology: official journal of the American Society of Clinical Oncology* 22, 3302-3308 (2004); published online EpubAug 15 (10.1200/JCO.2004.08.095).
5. L. Moja, L. Tagliabue, S. Balduzzi, E. Parmelli, V. Pistotti, V. Guarneri, R. D'Amico, Trastuzumab containing regimens for early breast cancer. *The Cochrane database of systematic reviews* 4, CD006243 (2012)10.1002/14651858.CD006243.pub2).
6. L. Carey, E. Winer, G. Viale, D. Cameron, L. Gianni, Triple-negative breast cancer: disease entity or title of convenience? *Nat Rev Clin Oncol* 7, 683-692 (2010); published online EpubDec (10.1038/nrclinonc.2010.154).
7. C. M. Perou, Molecular stratification of triple-negative breast cancers. *Oncologist* 16 Suppl 1, 61-70 (2011)10.1634/thooncologist.201-S1-61).
8. M. Kaucka, K. Plevova, S. Pavlova, P. Janovska, A. Mishra, J. Verner, J. Prochazkova, P. Krejci, J. Kotaskova, P. Ovesna, B. Tichy, Y. Brychtova, M. Doubek, A. Kozubik, J. Mayer, S. Pospisilova, V. Bryja, The Planar Cell Polarity Pathway Drives Pathogenesis of Chronic Lymphocytic Leukemia by the Regulation of B-Lymphocyte Migration. *Cancer Research* 73, 1491-1501 (2013); published online Epub-Mar 1 (Doi 10.1158/0008-5472can-12-1752).
9. C. Brockschmidt, H. Hirner, N. Huber, T. Eismann, A. Hillenbrand, G. Giamas, B. Radunsky, O. Ammerpohl, B. Bohm, D. Henne-Bruns, H. Kalthoff, F. Leithauser, A. Trauzold, U. Knippschild, Anti-apoptotic and growth-stimulatory functions of CK1 delta and epsilon in ductal adenocarcinoma of the pancreas are inhibited by IC261 in vitro and in vivo. *Gut* 57, 799-806 (2008); published online EpubJun (10.1136/gut.2007.123695).
10. I. C. Tsai, M. Woolf, D. W. Neklason, W. W. Branford, H. J. Yost, R. W. Burt, D. M. Virshup, Disease-associated casein kinase I delta mutation may promote adenomatous polyps formation via a Wnt/beta-catenin independent mechanism. *Int J Cancer* 120, 1005-1012 (2007); published online EpubMar 1 (10.1002/ijc.22368).

11. N. Rodriguez, J. Z. Yang, K. Hasselblatt, S. B. Liu, Y. L. Zhou, J. A. Rauh-Hain, S. K. Ng, P. W. Choi, W. P. Fong, N. Y. R. Agar, W. R. Welch, R. S. Berkowitz, S. W. Ng, Casin kinase I epsilon interacts with mitochondrial proteins for the growth and survival of human ovarian cancer cells. *Embo Molecular Medicine* 4, 952-963 (2012); published online EpubSep (DOI 10.1002/emmm.201101094).

12. H. Hirner, C. Gunes, J. Bischof, S. Wolff, A. Grothey, M. Kuhl, F. Oswald, F. Wegwitz, M. R. Bosl, A. Trauzold, D. Henne-Bruns, C. Peifer, F. Leithauser, W. Deppert, U. Knippschild, Impaired CK1 delta activity attenuates SV40-induced cellular transformation in vitro and mouse mammary carcinogenesis in vivo. *PloS one* 7, e29709 (2012) 10.1371/journal.pone.0029709).

13. J. K. Cheong, T. H. Nguyen, H. Wang, P. Tan, P. M. Voorhoeve, S. H. Lee, D. M. Virshup, IC261 induces cell cycle arrest and apoptosis of human cancer cells via CK1delta/epsilon and Wnt/beta-catenin independent inhibition of mitotic spindle formation. *Oncogene* 30, 2558-2569 (2011); published online EpubJun 2 (10.1038/onc.2010.627).

14. S. Y. Kim, I. F. Dunn, R. Firestein, P. Gupta, L. Wardwell, K. Repich, A. C. Schinzel, B. Wittner, S. J. Silver, D. E. Root, J. S. Boehm, S. Ramaswamy, E. S. Lander, W. C. Hahn, CK1epsilon is required for breast cancers dependent on beta-catenin activity. *PloS one* 5, e8979 (2010) 10.1371/journal.pone.0008979).

15. S. Foldynova-Trantirkova, P. Sekyrova, K. Tmejova, E. Brumovska, O. Bernatik, W. Blankenfeldt, P. Krejci, A. Kozubik, T. Dolezal, L. Trantirek, V. Bryja, Breast cancer-specific mutations in CK1epsilon inhibit Wnt/beta-catenin and activate the Wnt/Rac1/JNK and NFAT pathways to decrease cell adhesion and promote cell migration. *Breast Cancer Res* 12, R30 (2010)bcr2581 [pii] 10.1186/bcr2581).

16. M. Bibian, R. J. Rahaim, J. Y. Choi, Y. Noguchi, S. Schurer, W. Chen, S. Nakanishi, K. Licht, L. H. Rosenberg, L. Li, Y. Feng, M. D. Cameron, D. R. Duckett, J. L. Cleveland, W. R. Roush, Development of highly selective casein kinase 1delta/1epsilon (CK1delta/epsilon) inhibitors with potent antiproliferative properties. *Bioorganic & medicinal chemistry letters* 23, 4374-4380 (2013); published online EpubAug 1 (10.1016/j.bmcl.2013.05.075).

17. G. Finak, S. Sadekova, F. Pepin, M. Hallett, S. Meterissian, F. Halwani, K. Khetani, M. Souleimanova, B. Zabolotny, A. Omeroglu, M. Park, Gene expression signatures of morphologically normal breast tissue identify basal-like tumors. *Breast Cancer Res* 8, R58 (2006)10.1186/bcr1608).

18. J. S. Parker, M. Mullins, M. C. Cheang, S. Leung, D. Voduc, T. Vickery, S. Davies, C. Fauron, X. He, Z. Hu, J. F. Quackenbush, I. J. Stijileman, J. Palazzo, J. S. Marron, A. B. Nobel, E. Mardis, T. O. Nielsen, M. J. Ellis, C. M. Perou, P. S. Bernard, Supervised risk predictor of breast cancer based on intrinsic subtypes. *Journal of clinical oncology: official journal of the American Society of Clinical Oncology* 27, 1160-1167 (2009); published online EpubMar 10 (10.1200/JCO.2008.18.1370).

19. X. Zhang, S. Claerhout, A. Prat, L. E. Dobrolecki, I. Petrovic, Q. Lai, M. D. Landis, L. Wiechmann, R. Schiff, M. Giuliano, H. Wong, S. W. Fuqua, A. Contreras, C. Gutierrez, J. Huang, S. Mao, A. C. Pavlick, A. M. Froehlich, M. F. Wu, A. Tsimelzon, S. G. Hilsenbeck, E. S. Chen, P. Zuloaga, C. A. Shaw, M. F. Rimawi, C. M. Perou, G. B. Mills, J. C. Chang, M. T. Lewis, A renewable tissue resource of phenotypically stable, biologically and ethnically diverse, patient-derived human breast cancer xenograft models. *Cancer research* 73, 4885-4897 (2013); published online EpubAug 1 (10.1158/0008-5472.CAN-12-4081).

20. K. R. Brennan, A. M. Brown, Wnt proteins in mammary development and cancer. *J Mammary Gland Biol Neoplasia* 9, 119-131 (2004); published online EpubApr (10.1023/B:JOMG.0000037157.94207.33).

21. F. C. Geyer, M. Lacroix-Triki, K. Savage, M. Arnedos, M. B. Lambros, A. MacKay, R. Natrajan, J. S. Reis-Filho, beta-Catenin pathway activation in breast cancer is associated with triple-negative phenotype but not with CTNNB1 mutation. *Mod Pathol* 24, 209-231 (2011); published online EpubFeb (10.1038/modpathol.2010.205).

22. V. Bryja, G. Schulte, E. Arenas, Wnt-3a utilizes a novel low dose and rapid pathway that does not require casein kinase 1-mediated phosphorylation of Dv1 to activate beta-catenin. *Cell Signal* 19, 610-616 (2007); published online EpubMar (10.1016/j.cellsig.2006.08.011).

23. U. Knippschild, M. Kruger, J. Richter, P. Xu, B. Garcia-Reyes, C. Peifer, J. Halekotte, V. Bakulev, J. Bischof, The CK1 Family: Contribution to Cellular Stress Response and Its Role in Carcinogenesis. *Front Oncol* 4, 96 (2014) 10.3389/fonc.2014.00096).

24. P. Wend, S. Runke, K. Wend, B. Anchondo, M. Yesayan, M. Jardon, N. Hardie, C. Loddenkemper, I. Ulasov, M. S. Lesniak, R. Wolsky, L. A. Bentolila, S. G. Grant, D. Elashoff, S. Lehr, J. J. Latimer, S. Bose, H. Sattar, S. A. Krum, G. A. Miranda-Carboni, WNT10B/beta-catenin signalling induces HMGA2 and proliferation in metastatic triple-negative breast cancer. *EMBO molecular medicine* 5, 264-279 (2013); published online EpubFeb (10.1002/emmm.201201320).

25. B. Schade, R. Lesurf, V. Sanguin-Gendreau, T. Bui, G. Deblois, S. A. O'Toole, E. K. A. Millar, S. J. Zardawi, E. Lopez-Knowles, R. L. Sutherland, V. Giguere, M. Kahn, M. Hallett, W. J. Muller, beta-Catenin Signaling Is a Critical Event in ErbB2-Mediated Mammary Tumor Progression. *Cancer Research* 73, 4474-4487 (2013); published online EpubJul 15 (Doi 10.1158/0008-5472.Can-12-3925).

26. M. Moumen, A. Chiche, C. Decraene, V. Petit, A. Gandarillas, M. A. Deugnier, M. A. Glukhova, M. M. Faraldo, Myc is required for beta-catenin-mediated mammary stem cell amplification and tumorigenesis. *Mol Cancer* 12, 132 (2013); published online EpubOct 30 (10.1186/1476-4598-12-132).

27. H. Al-Hussaini, D. Subramanyam, M. Reedijk, S. S. Sridhar, Notch signaling pathway as a therapeutic target in breast cancer. *Molecular cancer therapeutics* 10, 9-15 (2011); published online Epub January (10.1158/1535-7163.MCT-10-0677).

28. C. Liu, Y. Li, M. Semenov, C. Han, G. H. Baeg, Y. Tan, Z. Zhang, X. Lin, X. He, Control of beta-catenin phosphorylation/degradation by a dual-kinase mechanism. *Cell* 108, 837-847 (2002); published online EpubMar 22 ( 29. J. I. Yook, X. Y. Li, I. Ota, C. Hu, H. S. Kim, N. H. Kim, S. Y. Cha, J. K. Ryu, Y. J. Choi, J. Kim, E. R. Fearon, S. J. Weiss, A Wnt-Axin2-GSK3beta cascade regulates Snail1 activity in breast cancer cells. *Nat Cell Biol* 8, 1398-1406 (2006); published online EpubDec (10.1038/ncb1508).

30. J. I. Yook, X. Y. Li, I. Ota, E. R. Fearon, S. J. Weiss, Wnt-dependent regulation of the E-cadherin repressor snail. *J Biol Chem* 280, 11740-11748 (2005); published online EpubMar 25 (10.1074/jbc.M413878200).

31. A. Bafico, G. Liu, L. Goldin, V. Harris, S. A. Aaronson, An autocrine mechanism for constitutive Wnt pathway activation in human cancer cells. *Cancer Cell* 6, 497-506 (2004); published online EpubNov (10.1016/j.ccr.2004.09.032).

32. M. J. Higgins, J. Basolga, Targeted therapies for breast cancer. *J Clin Invest* 121, 3797-3803 (2011); published online EpubOct (10.1172/JCI57152).

33. J. K. Choong, D. M. Virshup, Casein kinase 1: Complexity in the family. *The international journal of biochemistry & cell biology* 43, 465-469 (2011); published online EpubApr (10.1016/j.biocel.2010.12.004).

34. P. Polakis, Wnt signaling in cancer. *Cold Spring Harb Perspect Biol* 4, (2012); published online EpubMay (10.1101/cshperspect.a008052).

35. S. Y. Lin, W. Xia, J. C. Wang, K. Y. Kwong, B. Spohn, Y. Wen, R. G. Pestell, M. C. Hung, Beta-catenin, a novel prognostic marker for breast cancer: its roles in cyclin D1 expression and cancer progression. *Proc Natl Acad Sci USA* 97, 4262-4266 (2000); published online EpubApr 11 (10.1073/pnas.060025397).

36. W. H. Xu, Z. B, Liu, C. Yang, W. Qin, Z. M. Shao, Expression of dickkopf-1 and beta-catenin related to the prognosis of breast cancer patients with triple negative phenotype. *PLoS One* 7, e37624 (2012)10.1371/journal.pone.0037624).

37. A. M. Brown, Wnt signaling in breast cancer: have we come full circle? *Breast Cancer Res* 3, 351-355 (2001).

38. D. Wiederschain, S. Wee, L. Chen, A. Loo, G. Yang, A. Huang, Y. Chen, G. Caponigro, Y. M. Yao, C. Lengauer, W. R. Sellers, J. D. Benson, Single-vector inducible lentiviral RNAi system for oncology target validation. *Cell cycle* 8, 498-504 (2009); published online EpubFeb 1.

39. C. Fuerer, R. Nusse, Lentiviral vectors to probe and manipulate the Wnt signaling pathway. *PLoS One* 5, e9370 (2010)10.1371/journal.pone.0009370).

40. C. H. Mermel, S. E. Schumacher, B. Hill, M. L. Meyerson, R. Beroukhim, G. Getz, GISTIC2.0 facilitates sensitive and confident localization of the targets of focal somatic copy-number alteration in human cancers. *Genome Biol* 12, R41 (2011)gb-2011-12-4-r41 [pii]10.1186/gb-2011-12-4-r41).

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of treating cancer, comprising administering to a patient afflicted therewith an effective dose of a compound of formula (I)

wherein
each R is independently selected hydrogen or $(C_1-C_6)$ alkyl, or two R groups bonded to a nitrogen atom together with the nitrogen atom can form a 5-7 membered heterocyclyl optionally further comprising 1 or 2 heteroatoms selected from the group consisting of O, S, and NR', wherein R' is hydrogen or $(C_1-C_6)$alkyl;

$Ar^1$ is an aryl or a 5-membered or 6-membered heteroaryl, which is unsubstituted or is substituted with 1-3 independently selected halo, $(C_1-C_6)$alkyl, $(C_1-C_6)$fluoroalkyl, $(C_1-C_6)$alkoxyl, cyano, nitro, $C(=O)NR_2$, $OC(=O)NR_2$, $N(R)C(=O)OR$, $N(R)C(=O)R$, or $C(=O)OR$;

$Het^1$ is a monocyclic or bicyclic heteroaryl, which is unsubstituted or is substituted with 1-3 independently selected halo, $(C_1-C_6)$alkyl, $(C_1-C_6)$fluoroalkyl, $(C_1-C_6)$alkoxyl, cyano, nitro, $C(=O)NR_2$, $OC(=O)NR_2$, $N(R)C(=O)OR$, $N(R)C(=O)R$, or $C(=O)OR$;

or a pharmaceutically acceptable salt thereof;

wherein the cancer is a cancer with upregulated expression levels of both CK1δ and β-catenin; and wherein the breast cancer is of the triple negative subclass of breast cancers (TNBC) or is an HER+ breast cancer.

2. The method of claim 1, wherein the compound of formula (I) is SR-3029 or a pharmaceutically acceptable salt thereof.

* * * * *

UNITED STATES PATENT AND TRADEMARK OFFICE
CERTIFICATE OF CORRECTION

Page 1 of 1

PATENT NO. : 10,603,322 B2
APPLICATION NO. : 15/768257
DATED : March 31, 2020
INVENTOR(S) : Roush et al.

It is certified that error appears in the above-identified patent and that said Letters Patent is hereby corrected as shown below:

In the Specification

Column 1, Lines 12-16, the paragraph "STATEMENT OF GOVERNMENT SUPPORT" should be changed to:
-- STATEMENT OF GOVERNMENT LICENSE RIGHTS
This invention was made with government support under grant numbers CA175094 and MH074404 awarded by The National Institutes of Health. The government has certain rights in the invention. --

Signed and Sealed this
Fourteenth Day of July, 2020

Andrei Iancu
*Director of the United States Patent and Trademark Office*